United States Patent [19]

Kiesele et al.

[11] Patent Number: 5,198,092

[45] Date of Patent: * Mar. 30, 1993

[54] ELECTROCHEMICAL MEASURING CELL FOR DETERMINING AMMONIA OR HYDRAZINE IN A MEASURING SAMPLE

[75] Inventors: Herbert Kiesele, Lübeck; Uwe Kühn, Wesenberg; Stephan Haupt, Lübeck, all of Fed. Rep. of Germany

[73] Assignee: Drägerwerk Aktiengesellschaft, Lübeck, Fed. Rep. of Germany

[*] Notice: The portion of the term of this patent subsequent to Dec. 31, 2008 has been disclaimed.

[21] Appl. No.: 696,089

[22] Filed: May 6, 1991

Related U.S. Application Data

[63] Continuation-in-part of Ser. No. 507,755, Apr. 12, 1990, Pat. No. 5,076,904.

[30] Foreign Application Priority Data

Apr. 29, 1989 [DE] Fed. Rep. of Germany ....... 3914284

[51] Int. Cl.$^5$ .......................................... G01N 27/404
[52] U.S. Cl. ................... 204/402; 204/153.14; 204/153.17; 204/412; 204/415
[58] Field of Search ...................... 204/153.14, 153.17, 204/412, 415, 432, 402

[56] References Cited

U.S. PATENT DOCUMENTS 2,651,612  9/1953  Haller ................................. 204/431
2,898,282  8/1959  Flook et al. ..................... 204/153.16

Primary Examiner—T. Tung
Attorney, Agent, or Firm—Walter Ottesen

[57] ABSTRACT

The invention is directed to an electrochemical measuring cell for determining ammonia or hydrazine in a gaseous or liquid measuring sample. The measuring cell has at least one measuring electrode and at least one counter electrode which are disposed in an electrolyte chamber filled with a soluble electrolyte containing a cobalt salt dissolved therein. The electrolyte chamber is closed off in the direction facing toward the measuring sample by a permeable membrane. The measuring cell provides a selective ammonia measurement having the following advantages: a short response time, a linear response and a low tendency to drift. The electrodes of the measuring cell are so configured that the oxidation of the ammonia as a measurement reaction has no influence on the sensitivity of the measuring cell. For this purpose, at least the measuring electrode is provided with a coating containing cobalt oxide which is in direct contact with the electrolyte.

18 Claims, 1 Drawing Sheet

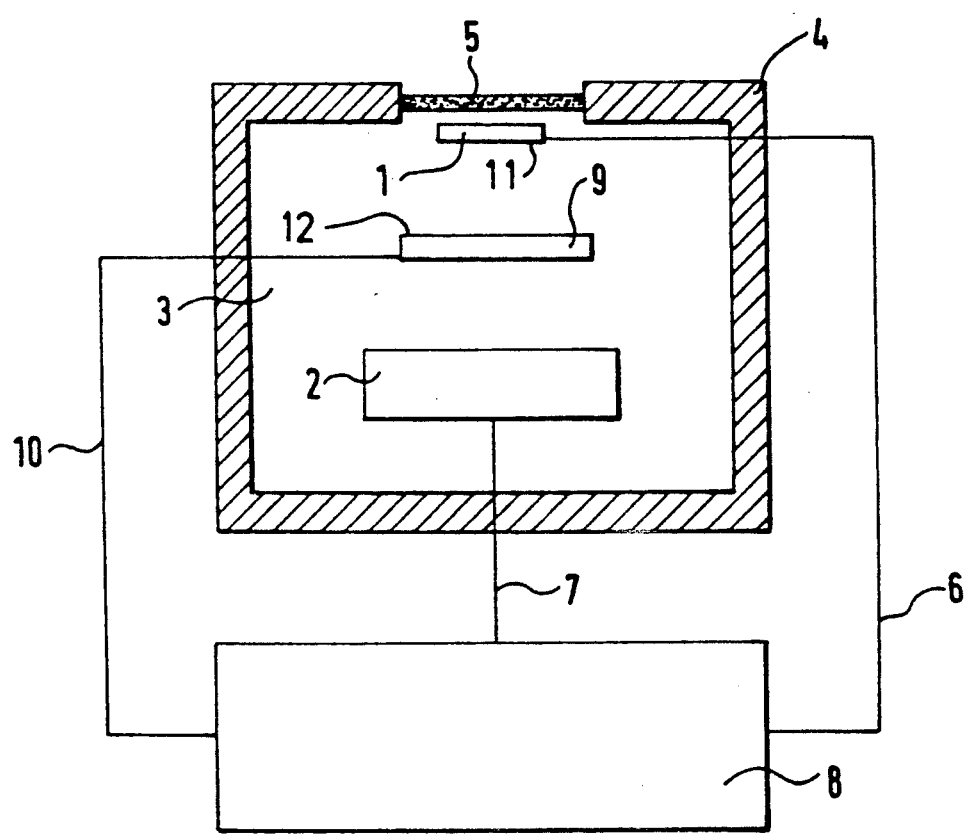

ELECTROCHEMICAL MEASURING CELL FOR DETERMINING AMMONIA OR HYDRAZINE IN A MEASURING SAMPLE

RELATED APPLICATION

This is a continuation-in-part of application Ser. No. 507,755, filed on Apr. 12, 1990, now U.S. Pat. No. 5,076,904, and entitled "Electrochemical Measuring Cell for Determining Ammonia or Hydrazine in a Measuring Sample".

FIELD OF THE INVENTION

The invention relates to an electrochemical measuring cell for determining ammonia or hydrazine in a fluid (gaseous or liquid) measuring sample. The measuring cell has at least one measuring electrode and at least one counter electrode which are arranged in an electrolyte chamber filled with a soluble electrolyte. The electrolyte chamber is closed off with respect to the measuring sample by a permeable membrane.

BACKGROUND OF THE INVENTION

An electrochemical measuring cell of this kind is disclosed in U.S. Pat. No. 3,649,505 and includes a pH-electrode as a measuring electrode which is used to measure hydrogen ions. This potentiometric measurement of an ammonia concentration requires a long time duration for a completed measuring reaction. The long time duration is needed for the adjustment of an equilibrium. In this time duration, the $NH_3$ to be detected and the water content of the electrolyte conjointly form $NH_4OH$ which, in turn, dissociates into $NH_4^+$ ions and $OH^-$ ions. The slow step determining the speed for this reaction is the adjustment of the equilibrium with the gas space or the adjustment of the equilibrium at the glass membrane.

The glass electrode required for the pH-measurement changes in the characteristic of the glass membrane in the course of its use so that drift phenomena occur. A stable reference potential is necessary for carrying out the pH-measurement and a displacement of this reference potential in the course of use likewise leads to drift phenomena. The known measuring cell responds to all gases influencing the pH-value of the electrolyte so that its selectivity for measurements in corresponding gas mixtures is not adequate.

SUMMARY OF THE INVENTION

It is an object of the invention to provide an electrochemical measuring cell of the kind described above which is improved so that a selective ammonia measurement is obtained providing the following: short response time, a linear response and a low tendency to drift. It is a further object of the invention to provide such an electrochemical measuring cell having electrodes which are so configured that the oxidation of the ammonia or hydrazine as a measurement reaction has no influence on the sensitivity of this measuring cell.

The electrochemical measuring cell of the invention is for determining ammonia or hydrazine in a fluid measuring sample. The measuring cell includes: a housing having an opening directed toward the sample to be measured and defining an electrolyte chamber; a soluble electrolyte contained in the chamber; a permeable membrane mounted on the housing for closing off the chamber; a measuring electrode and a counter electrode disposed in the chamber so as to be in spaced relationship to each other; and, the measuring electrode having a coating containing cobalt oxide and the coating being formed on the measuring electrode so as to be in direct contact with the electrolyte.

An advantage of the invention is essentially that the oxidation of the ammonia or hydrazine at the measuring electrode is catalyzed by the cobalt oxide coating so that no disturbing secondary products develop at the measuring electrode which could hinder an oxidation which follows. Furthermore, no blocking of the electrode occurs because of an electrochemically inert passive layer.

The measuring cell according to the invention affords the advantage that it offers a very good long-term stability and negligible drift. Also, very high concentrations of ammonia can be measured because of the catalytically effective oxide layer. These high concentrations are rendered harmless with respect to catalytic poisons or disadvantageous influences of the electrolyte for the operational capability of the measuring cell. Because of the coating of cobalt oxide, the oxidation of ammonia at the measuring electrode surface occurs so rapidly that the ammonia concentration at this electrode surface is practically zero. This results in a high concentration gradient between the measuring sample and the surface of the measuring electrode. In this way, the measuring cell reaction is returned to a transport-controlled reaction without restrictive reaction steps. This leads to a rapid response time and to a high sensitivity of the measuring cell. Gold, platinum or iridium can be selected as a carrier material for the electrode. The measuring cell of the invention is equally well suited for detecting hydrazine.

For producing a cobalt oxide coating, a carrier material of gold defining the electrode can, for example, be dipped into a cobalt nitrate solution or a cobalt acetate solution and cobalt oxide is then electrically deposited thereon. Potassium nitrate can be added to the cobalt solution as a conductive electrolyte.

Accordingly, the measuring electrode having the cobalt oxide coating is developed in place by an electrochemical process. The formation of the cobalt oxide coating affords the advantage that an intimate and durable bond is generated between the cobalt oxide and the carrier material and this facilitates the catalytic reaction of the cobalt oxide with the ammonia.

Another method for forming the cobalt oxide coating is to form the carrier material for the electrode from a cobalt-containing alloy which is then oxidized.

Carrier materials for electrochemically measuring ammonia can be used by applying the coating containing cobalt oxide. Without this coating, a surface passivation in the form of a nitride formation occurs whereby the measuring sensitivity is reduced to the point that the measuring cell is unusable. In this connection, reference may be made to the "Encyclopedia of Electrochemistry of the Elements", Volume 8, 1978, page 413.

With respect to the measuring cell of the invention, it is emphasized that there is no cross-sensitivity against carbon monoxide or hydrogen.

In order to generate a reference potential for determining ammonia or hydrazine, a reference electrode is introduced into the measuring cell having a potential which functions as a reference point for the measurement. It is advantageous to likewise provide such a reference electrode with a coating containing cobalt oxide. A measuring cell of this kind affords the advantage that it can be stored with short-circuited electrodes whereby it is immediately operationally ready because of the short warm-up time. Furthermore, the dependency of the residual current on temperature is minimized since the potential of the measuring electrode and of the reference electrode are influenced in the same manner by the temperature.

It is another object of the invention to provide a measuring cell of the kind described above wherein the response time is still shorter and sensitivity is further increased.

This improved performance is achieved in a further embodiment of the invention wherein a cobalt salt such as cobalt nitrate is added to the electrolyte to operate as a catalyzer. The cobalt salt operates catalytically in the electrolyte to regenerate the cobalt oxide coating which becomes damaged during operation of the measuring cell. In addition to regenerating the cobalt oxide coating, the cobalt salt in the electrolyte supports the catalytic reaction of the oxidation of ammonia or hydrazine at the measuring electrode to thereby increase the sensitivity and response speed of the cell.

When a working voltage of 600 mV is applied across the measuring and counter electrodes, the coating of cobalt oxide is spontaneously formed on the measuring electrode which becomes catalytically effective in the measuring cell. This coating always builds up to a layer thickness having a defined limit value because the layer is self-inhibiting.

The occurrence of electrical disturbances destroys the oxide layer for a short period of time. However, the cobalt nitrate in the electrolyte solution is sufficient to build up a new cobalt oxide layer. This action is very advantageous for the operational reliability of the measuring cell and is also effective when chemical disturbances occur.

As an example of this further embodiment, the measuring and counter electrodes can each be sinter electrodes made of iridium. Gold can be used in lieu of iridium but the latter has been found to be more easily produced. The electrolyte can include 3.5M $Ca(NO_3)$ and 0.1 mM $Co(NO_3)_2$ as a catalyst.

Lithium can be substituted for the calcium in the electrolyte. However, the concentration of lithium is so selected that water losses are minimized and a crystallization at low temperatures is prevented.

With respect to the catalyst, the cobalt nitrate concentration can be increased to 1 mM without affecting the sensing function. However, with higher concentrations of cobalt nitrate, disturbances can occur which are believed to be caused by reaction products generated on the counter electrode.

The measuring cell of this further embodiment can likewise be provided with a reference electrode which is preferably a sinter electrode made of iridium.

BRIEF DESCRIPTION OF THE DRAWING

The invention will now be described with reference to the single figure of the drawing which is a side elevation view, in section, of a measuring cell according to an embodiment of the invention.

DESCRIPTION OF THE PREFERRED EMBODIMENTS OF THE INVENTION

The electrochemical measuring cell includes an electrolyte 3 in which a measuring electrode 1, a counter electrode 2 and a reference electrode 9 are introduced. The electrodes (1, 9) have respective coatings (11, 12) containing cobalt oxide. The electrolyte 3 contains a cobalt salt such as cobalt nitrate dissolved therein and is closed off in a direction facing toward the measuring sample by a membrane 5 which is permeable to ammonia and which is attached to the housing 4 in a seal-tight manner. The measuring electrode 1, the counter electrode 2 and the reference electrode 9 are preferably sinter electrodes made of iridium and have respective measurement leads (6, 7, 10) which are passed through the housing 4 and connected to an evaluation device 8 for processing the measurement signals.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for determining ammonia or hydrazine in a fluid measuring sample, the measuring cell comprising:

a housing having an opening directed toward the sample to be measured and defining an electrolyte chamber;

a soluble electrolyte mixture comprising a cobalt salt dissolved therein to produce cobalt ions and being contained in said chamber;

a permeable membrane mounted on said housing for closing off said chamber;

a measuring electrode and a counter electrode disposed in said chamber so as to be in spaced relationship to each other;

said measuring electrode having a coating containing cobalt oxide and said coating being formed on said measuring electrode so as to be in direct contact with said electrolyte;

a reference electrode disposed in said electrolyte and having a coating formed thereon which likewise contains cobalt oxide; and, voltage supply means for applying a voltage across said electrodes.

2. The electrochemical measuring cell of claim 1, said measuring electrode and said reference electrode each including a carrier made of a noble metal and said coating being electrolytically deposited on said carrier.

3. An electrochemical measuring cell for determining ammonia or hydrazine in a fluid measuring sample, the measuring cell comprising:

a housing having an opening directed toward the sample to be measured and defining an electrolyte chamber;

a soluble electrolyte mixture comprising a cobalt salt dissolved therein to produce cobalt ions and being contained in said chamber;

a permeable membrane mounted on said housing for closing off said chamber;

a measuring electrode and a counter electrode disposed in said chamber so as to be in spaced relationship to each other;

said measuring electrode having a coating containing cobalt oxide and said coating being formed on said measuring electrode so as to be in direct contact with said electrolyte;

a reference electrode disposed in said electrolyte and having a coating formed thereon which likewise contains cobalt oxide;

voltage supply means for applying a voltage across said electrodes; and, said measuring electrode, said counter electrode and said reference electrode each being a sinter electrode made of iridium.

4. An electrochemical measuring cell for determining ammonia or hydrazine in a fluid measuring sample, the measuring cell comprising:
- a housing having an opening directed toward the sample to be measured and defining an electrolyte chamber;
- a soluble electrolyte mixture comprising a cobalt salt dissolved therein to produce cobalt ions and being contained in said chamber;
- a permeable membrane mounted on said housing for closing off said chamber;
- a measuring electrode and a counter electrode disposed in said chamber so as to be in spaced relationship to each other;
- said measuring electrode having a coating containing cobalt oxide and said coating being formed on said measuring electrode so as to be in direct contact with said electrolyte;
- voltage supply means for applying a working potential across said measuring electrode and said counter electrode of an amount sufficient to facilitate oxidation of the cobalt ions dissolved in said electrolyte which thereupon build up a deposit on said measuring electrode for regenerating said coating; and,
- said electrodes each being a sinter electrode made of iridium.

5. An electrochemical measuring cell for determining ammonia or hydrazine in a fluid measuring sample, the measuring cell comprising:
- a housing having an opening directed toward the sample to be measured and defining an electrolyte chamber;
- a soluble electrolyte mixture comprising a cobalt salt dissolved therein to produce cobalt ions and being contained in said chamber;
- a permeable membrane mounted on said housing for closing off said chamber;
- a measuring electrode and a counter electrode disposed in said chamber so as to be in spaced relationship to each other;
- said measuring electrode having a coating containing cobalt oxide and said coating being formed on said measuring electrode so as to be in direct contact with said electrolyte;
- voltage supply means for applying a working potential across said measuring electrode and said counter electrode of an amount sufficient to facilitate oxidation of the cobalt ions dissolved in said electrolyte which thereupon build up a deposit on said measuring electrode for regenerating said coating; and,
- said electrodes each being made of gold.

6. An electrochemical measuring cell for determining ammonia or hydrazine in a fluid measuring sample, the measuring cell comprising:
- a housing having an opening directed toward the sample to be measured and defining an electrolyte chamber;
- a soluble electrolyte mixture comprising a cobalt salt dissolved therein to produce cobalt ions and being contained in said chamber;
- a permeable membrane mounted on said housing for closing off said chamber;
- a measuring electrode and a counter electrode disposed in said chamber so as to be in spaced relationship to each other;
- said measuring electrode having a coating containing cobalt oxide and said coating being formed on said measuring electrode so as to be in direct contact with said electrolyte;
- voltage supply means for applying a working potential across said measuring electrode and said counter electrode of an amount sufficient to facilitate oxidation of the cobalt ions dissolved in said electrolyte which thereupon build up a deposit on said measuring electrode for regenerating said coating; and,
- said cobalt salt being cobalt nitrate.

7. An electrochemical measuring cell for determining ammonia or hydrazine in a fluid measuring sample, the measuring cell comprising:
- a housing having an opening directed toward the sample to be measured and defining an electrolyte chamber
- a soluble electrolyte mixture comprising a cobalt salt dissolved therein to produce cobalt ions and being contained in said chamber;
- a permeable membrane mounted on said housing for closing off said chamber;
- a measuring electrode and a counter electrode disposed in said chamber so as to be in spaced relationship to each other;
- said measuring electrode having a coating containing cobalt oxide and said coating being formed on said measuring electrode so as to be in direct contact with said electrolyte;
- voltage supply means for applying a working potential across said measuring electrode and said counter electrode of an amount sufficient to facilitate oxidation of the cobalt ions dissolved in said electrolyte which thereupon build up a deposit on said measuring electrode for regenerating said coating; and,
- said soluble electrolyte including calcium nitrate.

8. The electrochemical measuring cell of claim 7, wherein said cobalt salt is cobalt nitrate as a catalyst.

9. The electrochemical measuring cell of claim 8, wherein said electrodes are made of iridium.

10. The electrochemical measuring cell of claim 8, wherein said electrodes are made of gold.

11. An electrochemical measuring cell for determining ammonia or hydrazine in a fluid measuring sample, the measuring cell comprising:
- a housing having an opening directed toward the sample to be measured and defining an electrolyte chamber;
- a soluble electrolyte mixture comprising a cobalt salt dissolved therein to produce cobalt ions and being contained in said chamber;
- a permeable membrane mounted on said housing for closing off said chamber;
- a measuring electrode and a counter electrode disposed in said chamber so as to be in spaced relationship to each other;
- said measuring electrode having a coating containing cobalt oxide and said coating being formed on said measuring electrode so as to be in direct contact with said electrolyte;
- voltage supply means for applying a working potential across said measuring electrode and said counter electrode of an amount sufficient to facilitate oxidation of the cobalt ions dissolved in said electrolyte which thereupon build up a deposit on said measuring electrode for regenerating said coating; and, said soluble electrolyte including lithium nitrate.

12. The electrochemical measuring cell of claim 11, wherein said cobalt salt is cobalt nitrate.

13. The electrochemical measuring cell of claim 12, wherein said electrodes are made of iridium.

14. The electrochemical measuring cell of claim 12, wherein said electrodes are made of gold.

15. An electrochemical measuring cell for determining ammonia or hydrazine in a fluid measuring sample, the measuring cell comprising:
   a housing having an opening directed toward the sample to be measured and defining an electrolyte chamber;
   a soluble electrolyte mixture comprising a cobalt salt dissolved therein to produce cobalt ions and being contained in said chamber;
   a permeable membrane mounted on said housing for closing off said chamber;
   a measuring electrode and a counter electrode disposed in said chamber so as to be in spaced relationship to each other;
   said measuring electrode having a coating containing cobalt oxide and said coating being formed on said measuring electrode so as to be in direct contact with said electrolyte;
   voltage supply means for applying a working potential across said measuring electrode and said counter electrode of an amount sufficient to facilitate oxidation of the cobalt ions dissolved in said electrolyte which thereupon build up a deposit on said measuring electrode for regenerating said coating; and,
   said soluble electrolyte including calcium nitrate or lithium nitrate.

16. The electrochemical measuring cell of claim 15, wherein said cobalt salt is cobalt nitrate.

17. The electrochemical measuring cell of claim 16, wherein said electrodes are made of iridium.

18. The electrochemical measuring cell of claim 16, wherein said electrodes are made of gold.

* * * * *